United States Patent
Ryan et al.

(10) Patent No.: US 9,206,171 B2
(45) Date of Patent: *Dec. 8, 2015

(54) 6-{2-[1-(6-METHYL-3-PYRIDAZINYL)-4-PIPERIDINYL]ETHOXY}-3-ETHOXY-1,2-BENZISOXAZOLE BIS-DIHYDROGENPHOSPHATE SALT (1:2)

(71) Applicant: Biota Scientific Management Pty Ltd, Notting Hill, Victoria (AU)

(72) Inventors: Jane Ryan, Notting Hill (AU); Margaret Anne Butt, Whitfield (AU)

(73) Assignee: BIOTA SCIENTIFIC MANAGEMENT PTY LTD, Notting Hill, Victoria (AU)

( * ) Notice: Subject to any disclaimer, the term of this patent is extended or adjusted under 35 U.S.C. 154(b) by 95 days.

This patent is subject to a terminal disclaimer.

(21) Appl. No.: 14/023,280

(22) Filed: Sep. 10, 2013

(65) Prior Publication Data

US 2014/0179710 A1  Jun. 26, 2014

Related U.S. Application Data

(63) Continuation of application No. 12/994,633, filed as application No. PCT/AU2009/000663 on May 27, 2009, now Pat. No. 8,580,791.

(60) Provisional application No. 61/056,341, filed on May 27, 2008.

(51) Int. Cl.
| | |
|---|---|
| C07D 237/20 | (2006.01) |
| C07D 211/22 | (2006.01) |
| C07D 261/20 | (2006.01) |
| C07D 413/14 | (2006.01) |
| A61K 31/501 | (2006.01) |
| A61K 45/06 | (2006.01) |

(52) U.S. Cl.
CPC ............ *C07D 413/14* (2013.01); *A61K 31/501* (2013.01); *A61K 45/06* (2013.01)

(58) Field of Classification Search
CPC ... C07D 211/22; C07D 237/20; C07D 261/20

USPC ............................ 544/238; 546/210; 548/241
See application file for complete search history.

(56) References Cited

U.S. PATENT DOCUMENTS

| | | |
|---|---|---|
| 6,087,374 A | 7/2000 | Schladetzky et al. |
| 6,114,327 A | 9/2000 | Dunlap et al. |
| 6,358,971 B1 | 3/2002 | Ezquerra-Carrera et al. |

OTHER PUBLICATIONS

Jordan, V. C. Nature Reviews: Drug Discovery, 2, 2003, 205.*
Andries, et al. Antimicrobial Agents and Chemotherapy, 36(1), 1992, 100-107.*
Hackam, et al. JAMA, 296(14), 2006, 1731-1732.*
Chilean Office Action issued in corresponding Chilean Application No. 1315-2010.

* cited by examiner

*Primary Examiner* — Douglas M Willis
(74) *Attorney, Agent, or Firm* — B. Aaron Schulman, Esq.; Stites & Haribison, PLLC

(57) ABSTRACT

This invention relates to antiviral agents, in particular to salts useful in the treatment of infections caused by Picornaviridae, such as human rhinovirus (HRV) and methods for their preparation. In one embodiment, the invention relates to a bis-dihydrogenphophate salt having the formula:

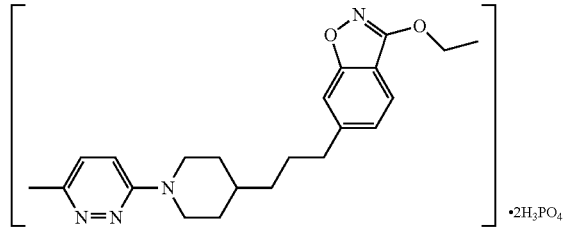

The invention also relates to the use of these salts in the treatment of picornavirus infections. The salts of this invention are especially suitable for use in the treatment of HRV, however it is to be understood that the invention is also applicable to other viruses of the picornavirus family.

11 Claims, 9 Drawing Sheets

(a)

(b)

6-{2-[1-(6-METHYL-3-PYRIDAZINYL)-4-PIPERIDINYL]ETHOXY}-3-ETHOXY-1,2-BENZISOXAZOLE BIS-DIHYDROGENPHOSPHATE SALT (1:2)

FIELD OF THE INVENTION

This invention relates to antiviral agents, in particular to salts useful in the treatment of infections caused by Picornaviridae, such as human rhinovirus (HRV) and methods for their preparation. The invention also relates to the use of these salts in the treatment of picornavirus infections. The salts of this invention are especially suitable for use in the treatment of HRV, however it is to be understood that the invention is also applicable to other viruses of the picornavirus family.

BACKGROUND OF THE INVENTION

Human rhinoviruses (HRV) are particular picornaviruses and are the most common infectious viral agents of the respiratory system. Indeed, they are the primary cause of the "common cold". The virus particles consist of a modular protein shell (the capsid) which encloses a short single strand of RNA.

One particular anti-picornavirus compound, which functions as a capsid-binding inhibitor and has been the subject of recent human clinical trials, is 4-[2-[1-(6-methyl-3-pyridazinyl)-4-piperidinyl]-ethoxy]benzoate—otherwise known as "Pirodavir". Pirodavir, being lipophilic, displays poor aqueous solubility and is often formulated with a cyclodextrin host. The resultant complex is more soluble in aqueous media, and allows delivery of the drug through such means as a nasal spray. It has, however, been shown that facile endogenous cleavage of the ester moiety in pirodavir leads to poor bioavailability of the molecule regardless of the chosen excipient. Furthermore, and in addition to cost, cyclodextrin host molecules have been shown to be otherwise disadvantageous in the formulation of pharmaceuticals (*Int. J. Pharm.*, 2002, 246, 25-35). Another promising anti-picornavirus compound, "Pleconaril", has been shown to interact adversely with patients using oral contraceptive formulations.

Clearly there is a need for an anti-picornavirus compound which displays desirable aqueous solubility properties, is stable under physiological conditions and has few adverse interactions. Additionally it is desirable that such a compound would be relatively easy to form and would be stable on storage in solid and solution form.

SUMMARY OF THE INVENTION

W02002/50045 discloses a novel class of antiviral compounds that were found to exhibit particularly favourable anti-picornoviral properties. It has now been surprisingly discovered that two particular acid addition salts, namely the phosphate and sulfate, of compound 35 of Table 3 of W02002/50045, offer particular advantage over other compounds currently proposed for the treatment of picornarviruses. Compound 35 (the 'free base'—represented by formula I below) has been shown to display potent activity against both HRV2 ($IC_{50}$ 0.001 [1.g/mL) and HRV14 ($IC_{50}$ 0.005 ug/mL). These tests were conducted using dimethylsulfoxide (DMSO) as the carrier solvent. The chemical name given to the compound of formula I is 6-{2-[1-(6-methyl-3-pyridazinyl)-4-piperidinyl]ethoxy}-3-ethoxy-1,2-benzisoxazole.

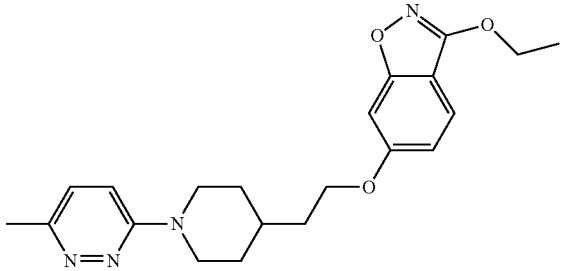

Particularly preferred stoichiometric forms of the acid addition salts of the free base (formula I) in accordance with the invention are:

a) the acid addition salt of phosphoric acid (2 equivalents) with the free base; and b) the acid addition salt of sulfuric acid (1 equivalent) with the free base.

Accordingly in one aspect the invention provides the phosphoric acid (2 eq) addition salt of the free base of the compound of formula I.

In another aspect the invention provides the sulfuric acid (1 eq) addition salt of the free base of the compound of formula I.

These salts advantageously have the following properties:

a) they display similar potent biological activity to the free base (for example $EC_{50}$ vs human rhinovirus is 14.4 nM for free base of compound of formula I and is 17.7 nM for phosphoric acid (2 eq) addition salt of free base of compound of formula I);

b) they have substantially greater aqueous solubility over other salts of the free base as well as the free base itself;

c) they form readily and are easy to isolate; and d) they crystallise readily, and those crystalline salts are stable both in the mother liquor and in isolated form.

These properties are recognised as being particularly desirable for a salt of the free base of a biologically active molecule to have, to assist with handling, formulation, etc.

In another aspect the invention provides pharmaceutical compositions comprising either or both of the salts and one or more carriers.

In another aspect the invention provides a method of forming the phosphoric acid addition salt comprising the step of reacting the free base with phosphoric acid. Preferably the free base is contacted with approximately 2 molar equivalents of phosphoric acid, more preferably between about 1.8 and 2.2 molar equivalents of phosphoric acid.

In another aspect the invention provides a method of forming the sulfuric acid addition salt comprising the step of reacting the free base with sulfuric acid. Preferably the free base is contacted with approximately 1 molar equivalent of sulfuric acid, more preferably between about 0.8 and 1.2 molar equivalents of sulfuric acid.

In another aspect the present invention provides a method of treating a picornavirus infection in a subject in need thereof comprising administering either or both of the salts.

In another aspect the present invention provides a method of preventing a picornavirus infection in a subject in need thereof comprising administering either or both of the salts.

In another aspect the present invention provides the use of either or both of the salts in the manufacture of a medicament for the treatment of a picornavirus infection in a subject in need thereof.

In another aspect the present invention provides the use of either or both of the salts in the manufacture of a medicament for the prevention of a picornavirus infection in a subject in need thereof.

DETAILED DESCRIPTION OF THE INVENTION

Figure 1:
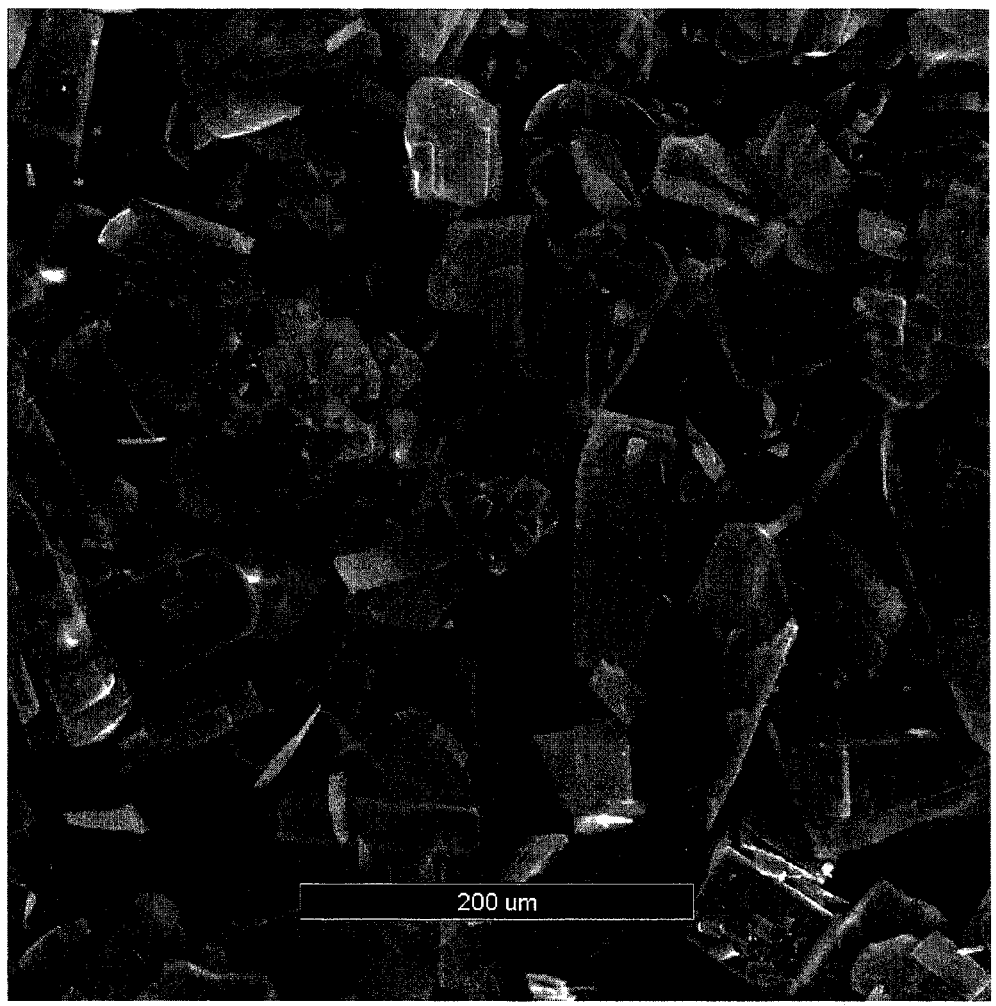
FIG. 1 is an image obtained using Scanning Electron Microscopy (SEM), with scale, of crystals of the phosphoric acid (2 eq) addition salt of the compound of formula I in accordance with a preferred embodiment of the invention.
Figure 2:
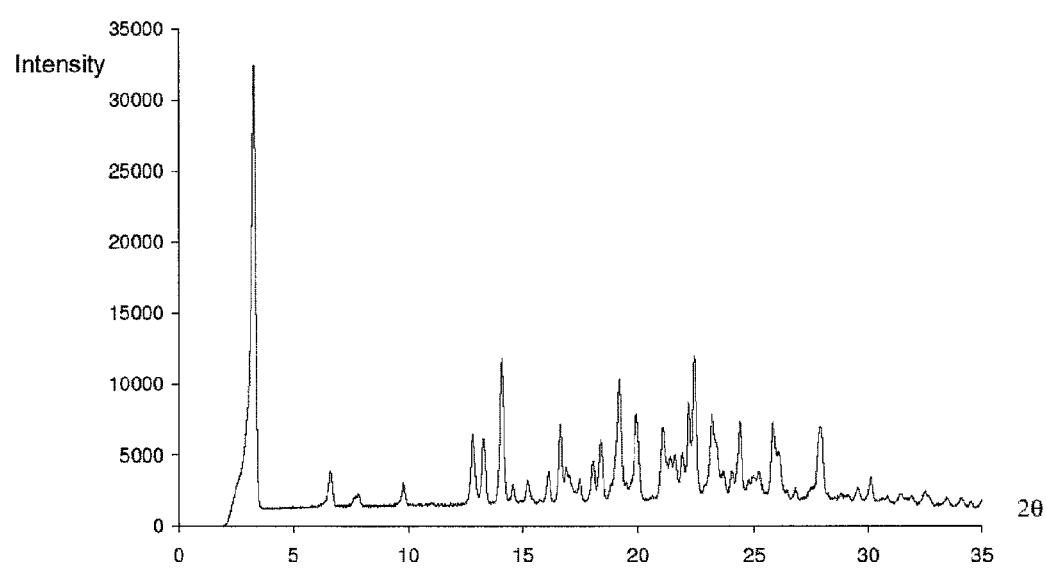
FIG. 2 is an X-Ray Powder Diffraction spectrum of the phosphoric acid (2 eq) addition salt of the compound of formula I in accordance with a preferred embodiment of the invention. The calculated 2θ peak values (±0.2°) are 3.3°, 6.7°, 12.8°, 13.3°, 14.1°, 19.2°, 20.0°, 21.1° and 22.4°.
Figure 3:
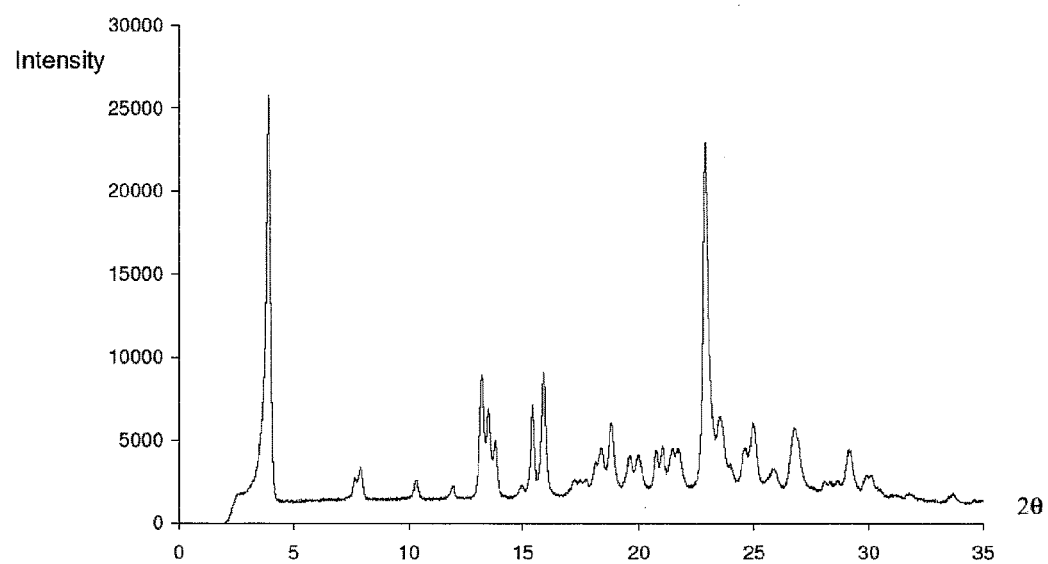
FIG. 3 is an X-Ray Powder Diffraction spectrum of the sulfuric acid (1 eq) addition salt of the compound of formula I in accordance with a preferred embodiment of the invention. The calculated 2θ peak values (±0.2°) are 3.3°, 6.7°, 13.2°, 15.5°, 15.9°, 18.9° and 22.9°.

Without wishing to be bound by theory, it is believed that of the nitrogen atoms present within the compound of formula I, only the piperidinyl nitrogen atom is readily protonated by an acid.

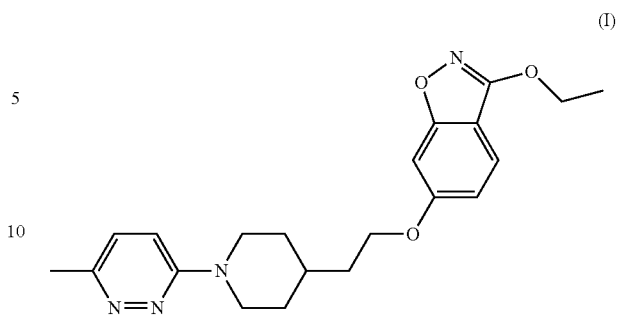

(I)

The other two basic nitrogen atom containing moieties within the molecule (being the benzisoxazolyl and pyridazinyl) are relatively weak bases, and it was believed that only reaction of either of these groups with a strong acid would produce a stable acid addition salt. On the other hand, it was also believed that the free base compound is sensitive to the action of strong acids, which presented another challenge to increasing the aqueous solubility of the free base—being achieving a balance between stable salt formation and degradation of the molecule.

It has now been surprisingly discovered that the reaction of the free base (formula I) with approximately 1 molar equivalent of sulfuric acid produces the monosulfate salt of the bis-protonated free base (formula II) remarkably without any observed degradation of the molecule. As used herein this addition salt is referred to as 6-{2-[1-(6-methyl-3-pyridazinyl)-4-piperidinyl]ethoxy}-3-ethoxy-1,2-benzisoxazole sulfate salt (1:1). The term "(1:1)" denotes the molar ratio of the bis-protonated conjugate acid of the free base of formula I to sulfate di-anion.

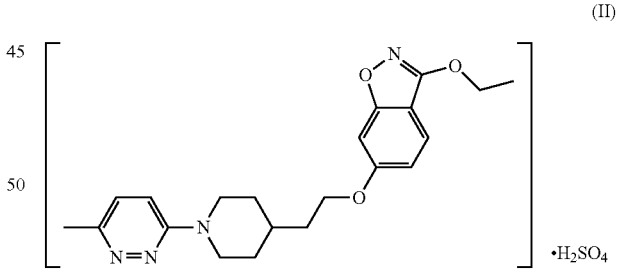

(II)

Furthermore, it has been surprisingly discovered that the reaction of the free base (formula I) with approximately 2 molar equivalents of phosphoric acid produces the bis-dihydrogenphosphate salt of the bis-protonated free base (formula III), again without any observed degradation. As used herein this addition salt is referred to as 6-{2-[1-(6-methyl-3-pyridazinyl)-4-piperidinyl]ethoxy}-3-ethoxy-1,2-benzisoxazole bis-dihydrogenphosphate salt (1:2). The term "(1:2)" denotes the molar ratio of the bis-protonated conjugate acid of the free base of formula I to dihydrogenphosphate anion.

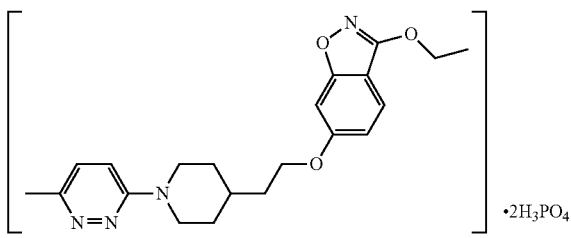

(III)

Whilst it may be the case that a given salt of a given active compound might display one or more properties which make it suitable for use as a pharmaceutical, what is particularly surprising about the since discovered properties of these two salts is that they substantially outperform other salts of the compound of formula I.

Of the reaction products formed from reaction of the free base of formula I with the following acids: acetic acid; citric acid; benzoic acid; fumaric acid; D-gluconic acid; hydrobromic acid; hydrochloric acid; maleic acid; nitric acid; oxalic acid; phosphoric acid; sulfuric acid; L-(+)-tartaric acid; toluenesulfonic acid; and methanesulfonic acid, only the salts formed from: nitric acid; phosphoric acid; sulfuric acid; hydrochloric acid; oxalic acid; and L-(+)-tartaric acid were demonstrated to produce salts or co-crystals of the free base which would furthermore potentially be suitable for pharmaceutical use.

The acid addition salt formed from the reaction of nitric acid with the free base of formula I displayed sub-optimal aqueous solubility. The product formed from contacting the free base of formula I with tartaric acid was subsequently shown to be a substantially co-crystalline compound, and not the desired acid addition salt.

The following techniques were used to characterise the acid addition salts and determine their solubility and stability:
a) Visual inspection;
b) Raman spectroscopy (to determine salt/co-crystal formation);
c) X-Ray Powder Diffraction spectroscopy (to determine the crystallinity of the product);
d) High Performance Liquid Chromatography (HPLC) analysis (reverse phase; to determine by-product formation);
e) Differential Scanning calorimetry (to determine melting point/decomposition temperature);
f) Elemental analysis (to determine purity/hygroscopicity);
g) Solubility determination (wherein 10 mg of the salt was contacted with a limited quantity of water for a time, and under conditions, such that solid necessarily remained and could be filtered off before the concentration of the saturated solution could be determined using HPLC);
h) Four week storage under different stress conditions (25° C. dry, 25° C. with 75% relative humidity (rh), 25° C. with 90% rh, 40° C. dry, 40° C. with 75% rh, 40° C. with 90% rh) including non-invasive characterisation by Near Infrared spectroscopy and Raman spectroscopy during the test as well as HPLC analysis at completion of the test.

Further details of the characterisation methods and parameters are provided in Example 5.

Table 1 shows comparative results which have been obtained for the acid addition salts of the free base of formula I. The darkened cells indicate results which disfavour the use of that salt as a pharmaceutical. As can be seen, salts 2 and 4 significantly outperform the other salts with respect to aqueous solubility and storage stability. The results of elemental analysis of the 2:1 oxalic acid:free base salt were not in agreement with the predicted results, and accordingly the slightly higher solubility of 1873 mg/mL was discounted as a meaningful result.

TABLE 1

| Salt | Acid (stoichiometry base:acid) | by-product? (HPLC) | Elemental Analysis (in agreement with calculated composition) | Solubility | Stability |
| --- | --- | --- | --- | --- | --- |
| 1 | HCl (1:1) | No | Yes | 835 µg/mL (pH 1.93) | isolated salt: slow morphological change at 25° C./90% rh isolated salt: fast morphological change at 40° C./90% rh |
| 2 | H$_2$SO$_4$ (1:1) | No | Yes | 1348 µg/mL (pH 1.99) | no degradation/change under all conditions not hygroscopic |
| 3 | H$_3$PO$_4$ (1:1) | No | Yes | 462 µg/mL (pH 2.12) | no degradation/change under all conditions not hygroscopic |
| 4 | H$_3$PO$_4$ (1:2) | No | Yes | 1384 µg/mL (pH 1.78) | no degradation/change under all conditions not hygroscopic |
| 5 | HO$_2$CCO$_2$H (1:1) | Yes | Yes | 625 µg/mL (pH 2.00) | isolated salt: morphological change at 25° C./90% rh not hygroscopic |
| 6 | HO$_2$CCO$_2$H (1:2) | Yes | No | 1873 µg/mL (pH 1.94) | hygroscopic under conditions of 75% rh and 90% rh |

Without wishing to be bound by theory, whilst two of the three basic nitrogen containing moieties on the compound of formula I are relatively weak it would appear that their participation in salt formation does not predicate the use of a necessarily strong acid. Phosphoric acid is a weaker acid than other inorganic acids such as sulfuric, hydrochloric and nitric acid. Nonetheless, and quite surprisingly, the phosphoric acid addition salt (salt 4 of Table 1) has been demonstrated to be not only crystalline, but also stable under a range of conditions. In fact, as can be seen in Table 1, the stability of the salt formed with hydrochloric acid (salt 1 of Table 1) was inferior to the salt formed with phosphoric acid (salt 4 of Table 1).

An additionally surprising result is that double protonation of the free base affords a product (salts of both formulae II and III) which displays greater stability than the product of single protonation of the free base by hydrochloric acid.

Furthermore, it would appear that the solubility of the bis-dihydrogenphosphate salt of formula III is greater than would have been predicted from extrapolation of the solubility of the mono-dihydrogenphosphate salt (salt 3 of Table 1).

The stability of the bis-dihydrogenphosphate salt has been tested using the test parameters of
  i) Appearance
  ii) Water content
  iii) Assay (Anhydrous basis)
  iv) Related Compounds (Reported as Maximum Individual)
  v) Related Compounds (Total)

The specifications for the bis-dihydrogenphosphate salt are shown in Table 2. The characterisation methods, parameters and exemplary HPLC assay data are provided in Example 5.

TABLE 2

Bis-dihydrogenphosphate salt specifications

| Test | Specification |
|---|---|
| 1. Appearance | Yellow free flowing powder. |
| 2. Identification (Infrared Spectrum) | The infrared spectrum of the sample exhibits maxima at the same wavelengths as that of a similar preparation of the reference standard. |
| 3. HPLC Assay | 95.0% to 105.0% (anhydrous, solvent free). |
| 4. Related Substances (HPLC) | i. Single maximum impurity should not be more than 0.5%. ii. Total impurities should not exceed 1.0%. |
| 5. Water Content (Karl Fischer) | Not more than 5.0%. |
| 6. Residual Solvents by GC | Isopropanol: Not more than 0.5% Acetone: Not more than 0.5% |

Two batch samples of the bis-dihydrogenphosphate salt were stored in the dark at 25° C./60% relative humidity for 12 months (Trial 1, Batch 1) and 36 months (Trial 2, Batch 2), respectively. Both batch samples were also stored in the dark under accelerated conditions at 40° C./75% relative humidity for 6 months. Samples were tested at appropriate intervals. The trials were performed in amber glass bottles equivalent to the full scale primary packaging unit.

Figure 4:
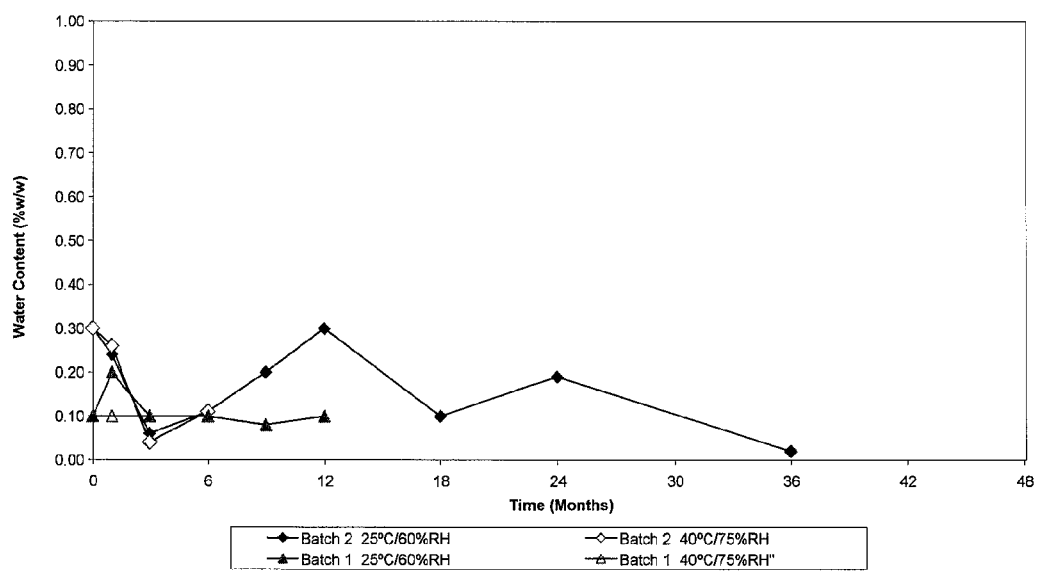
FIG. 4 shows the water content results obtained for trial 1 and trial 2 as described in Tables 3 and 4 for the bis-dihydrogenphosphate salt in accordance with a preferred embodiment of the invention.
Figure 5:
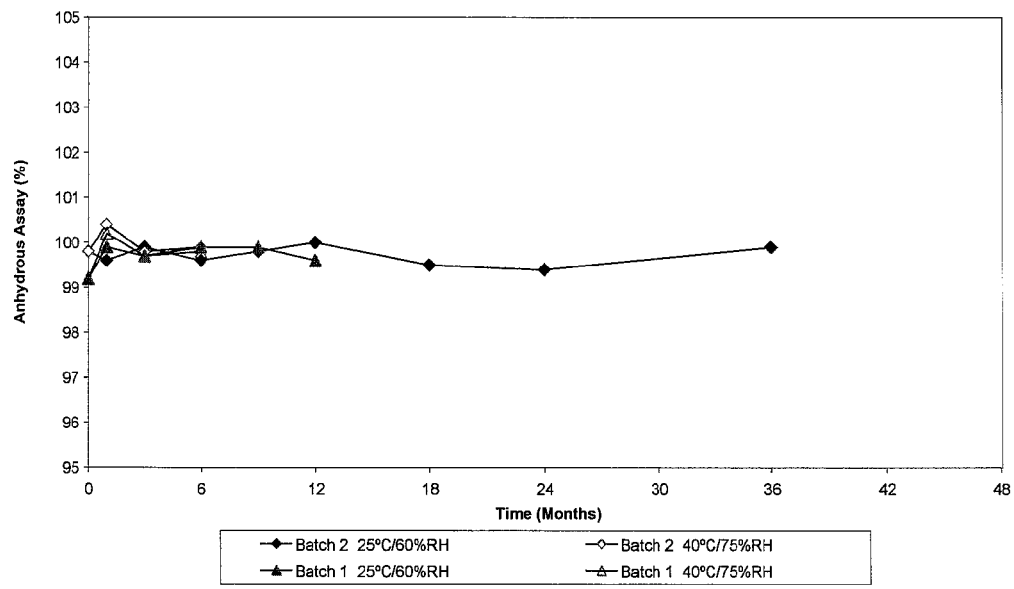
FIG. 5 shows the anhydrous assay results obtained for trial 1 and trial 2 as described in Tables 3 and 4 for the bis-dihydrogenphosphate salt in accordance with a preferred embodiment of the invention.
Figure 6:
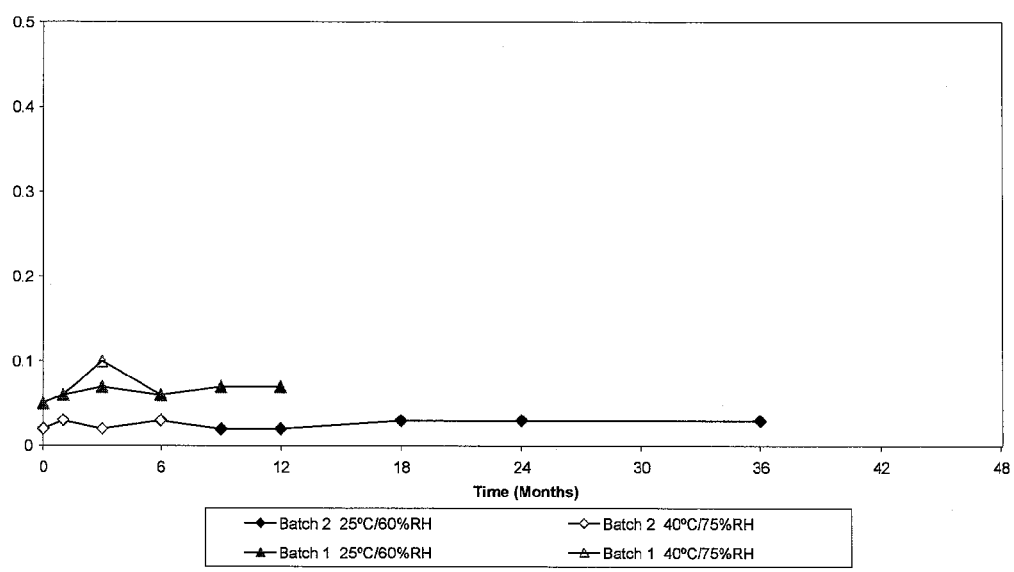
FIG. 6 shows the total related substance results obtained for trial 1 and trial 2 as described in Tables 3 and 4 for the bis-dihydrogenphosphate salt in accordance with a preferred embodiment of the invention.
Figure 7:
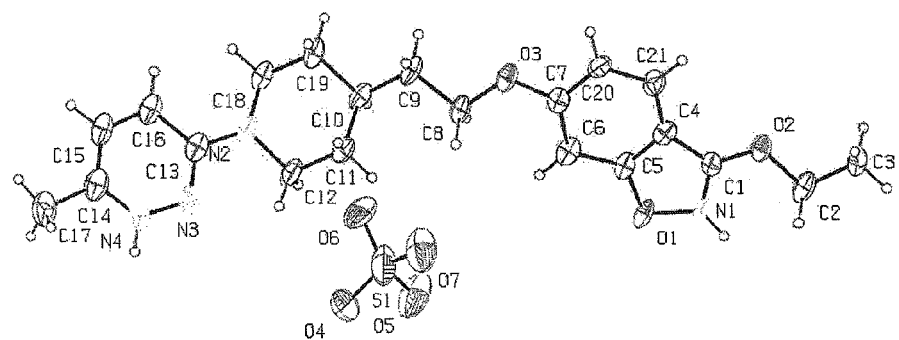
FIG. 7 is an x-ray crystal structure of the monosulfate salt in accordance with a preferred embodiment of the invention (a) shows an asymmetric unit (ORTEP drawing showing 30% probability ellipsoids) and (b) shows packing down the b-axis.
Figure 7:
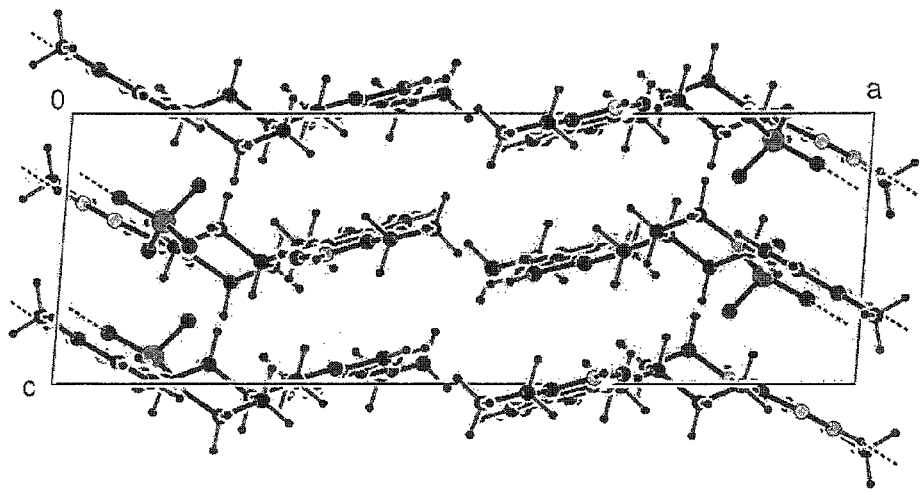
Figure 8:
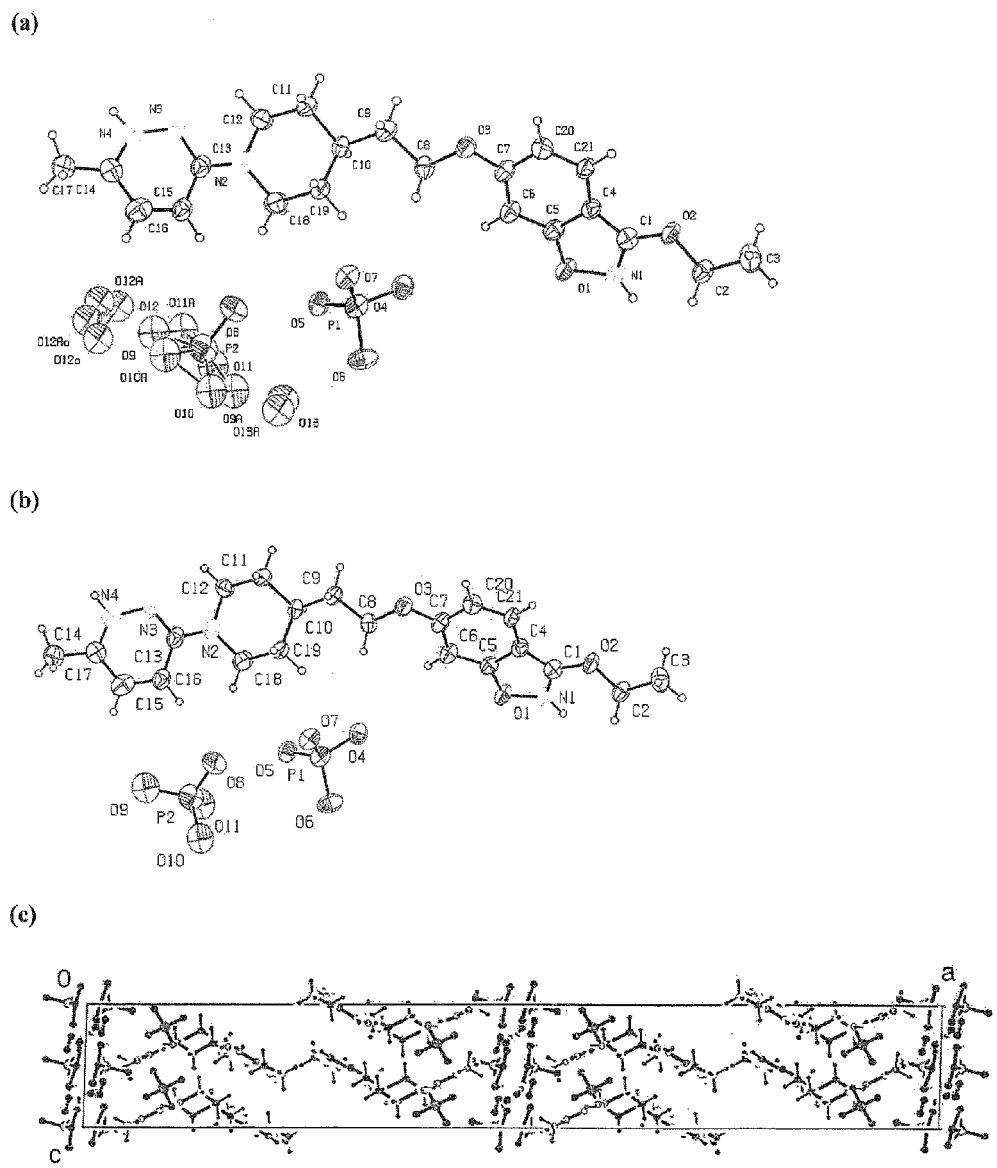
FIG. 8 is an x-ray crystal structure of the bis-dihydrogenphosphate salt in accordance with a preferred embodiment of the invention (a) shows an asymmetric unit showing the $H_2PO_4$ and $H_2O$ disorder (ORTEP drawing showing 30% probability ellipsoids) (b) shows an asymmetric unit removed $H_2O$ molecules and $H_2PO_4$ disorder (ORTEP drawing showing 30% probability ellipsoids) (c) shows packing down the b-axis.

The results demonstrate the long term stability of the bis-dihydrogenphosphate salt as shown in Table 3 (Trial 1) and Table 4 (Trial 2) and FIGS. 4 to 6.

TABLE 3

Twelve month stability data for bis-dihydrogenphosphate salt (Trial 1, Batch 1)

| Storage Condition | Storage Time (Months) | Appearance[1] | Water Content (%) | Assay (HPLC) (% on Anhydrous Basis) | Related Substances (Major by HPLC) (Area %) | Related Substances (Total by HPLC) (Area %) |
|---|---|---|---|---|---|---|
| Initial | 0 | Complies | 0.1 | 99.2 | 0.02 (RRT1.45) | 0.05 |
| 25° C. 60% RH | 1 | Complies | 0.2 | 99.9 | 0.01 (RRT0.20, 0.25, 0.34, 0.53, 1.45, 1.95) | 0.06 |
| | 3 | Complies | 0.1 | 99.7 | 0.02 (RRT0.35, 1.46) | 0.07 |
| | 6 | Complies | 0.1 | 99.9 | 0.02 (RRT1.43, 2.02) | 0.06 |
| | 9 | Complies | 0.1 | 99.9 | 0.02 (RRT0.34) | 0.07 |
| | 12 | Complies | 0.1 | 99.6 | 0.02 (RRT1.46, 1.97) | 0.07 |
| 40° C. 75% RH | 1 | Complies | 0.1 | 100.2 | 0.02 (RRT1.46) | 0.06 |
| | 3 | Complies | 0.1 | 99.7 | 0.03 (RRT1.45) | 0.10 |
| | 6 | Complies | 0.1 | 99.8 | 0.02 (RRT1.46) | 0.06 |

[1]Complies = Yellow free flowing powder. Packaging integral.

TABLE 4

Thirty-six month stability data for bis-dihydrogenphosphate salt (Trial 2, Batch 2)

| Storage Condition | Storage Time (Months) | Appearance[1] | Water Content (%) | Assay (HPLC) (% on Anhydrous Basis) | Related Substances (Major by HPLC) (Area %) | Related Substances (Total by HPLC) (Area %) |
|---|---|---|---|---|---|---|
| Initial | 0 | Complies | 0.3 | 99.8 | 0.02 (RRT1.45) | 0.02 |
| 25° C. 60% RH | 1 | Complies | 0.2 | 99.6 | 0.03 (RRT1.45) | 0.03 |
| | 3 | Complies | 0.1 | 99.9 | 0.02 (RRT1.46) | 0.02 |
| | 6 | Complies | 0.1 | 99.6 | 0.03 (RRT1.46) | 0.03 |
| | 9 | Complies | 0.2 | 99.8 | 0.02 (RRT1.45) | 0.02 |
| | 12 | Complies | 0.3 | 100.0 | 0.02 (RRT 1.47) | 0.02 |

TABLE 4-continued

Thirty-six month stability data for bis-dihydrogenphosphate salt (Trial 2, Batch 2)

| Storage Condition | Storage Time (Months) | Appearance[1] | Water Content (%) | Assay (HPLC) (% on Anhydrous Basis) | Related Substances (Major by HPLC) (Area %) | Related Substances (Total by HPLC) (Area %) |
|---|---|---|---|---|---|---|
| | 18 | Complies | 0.1 | 99.5 | 0.03 (RRT1.45) | 0.03 |
| | 24 | Complies | 0.2 | 99.4 | 0.03 (RRT1.44) | 0.03 |
| | 36 | Complies | 0.0 | 99.9 | 0.03 (RRT1.45) | 0.03 |
| 40° C. 75% RH | 1 | Complies | 0.3 | 100.4 | 0.03 (RRT1.45) | 0.03 |
| | 3 | Complies | 0.0 | 99.8 | 0.02 (RRT1.46) | 0.02 |
| | 6 | Complies | 0.1 | 99.9 | 0.03 (RRT1.46) | 0.03 |

[1]Complies = Yellow free flowing powder. Packaging integral.

Whilst the acid addition salts of the present invention are described with reference to a seemingly exact molar ratio of the anion to cation, it is understood that the acid addition salts of the present invention may comprise a mixture of the salt, free base and where appropriate excess acid depending on the reaction conditions used to form the salt. For example, if less than 1 molar equivalent of sulfuric acid (for example 0.7 eq) is reacted with the free base of formula I, the isolated product of the reaction is likely to contain a certain proportion of the salt of formula II, together with a certain proportion of the free base of formula I. The mixture may, however, still exhibit many of the advantageous properties of the salt formed using 1 molar equivalent of the acid. Likewise, if greater than 2 molar equivalents of phosphoric acid (for example 2.6 eq) is reacted with the free base of formula II, the isolated product is likely to contain a certain proportion of the salt of formula III, together with a certain proportion of excess phosphoric acid. The mixture may, however, still exhibit many of the advantageous properties of the salt so-formed using 2 molar equivalents of the acid. It is understood that such mixtures fall within the scope of the invention. Accordingly in a preferred embodiment of the invention there is provided a mixture comprising, more preferably consisting essentially of, the acid addition salt of the compound of formula I.

The present invention also provides a method of forming the salt of formula II, comprising contacting the free base of formula I with sulfuric acid. The present invention also provides a method of forming the salt of formula III, comprising contacting the free base of formula I with phosphoric acid. It is understood that in the formation of the salts, it is possible that the final product will be contaminated with salts of stoichiometry which is different to the stoichiometry of the salts of formulae II and III. In some embodiments, the salt of formula II is formed by contacting the free base with between 0.5 and 1.5 molar equivalents (preferably between 0.9 and 1.1 molar equivalents) of sulfuric acid. In some embodiments, the salt of formula III is formed by contacting the free base with between 1.5 and 2.5 molar equivalents (preferably between 1.8 and 2.2 molar equivalents) of phosphoric acid. In each case, it is preferable to use a reaction solvent or solvents which allow complete dissolution of the free base and sulfuric/phosphoric acid, but which are poor solvents for the product salt of formula II/III. Isopropanol is preferable for the formation of the bis-dihydrogenphosphate salt, whilst ethanol and less so methanol provide examples of other alternatives. It is understood that both phosphoric acid and sulfuric acid often contain some quantity of water. Judicious choice of the reaction solvent allows for the facile separation of the salt from the mother liquor and is a technique well known in the art. Alternatively, it may be possible to avoid the use of a solvent through the use of either neat sulfuric acid or neat phosphoric acid. In any event, it is understood that the skilled chemist would readily modify the temperature of the reaction mixture during and/or after reaction in order to optimise the formation of the salt and/or optimise the recovery of the salt from the reaction mixture following salt formation. For example the free base and acid may be initially heated to effect dissolution and/or facilitate thorough mixing, before the reaction mixture is cooled to reduce the amount of the salt that remains in solution.

Whilst it is preferable that the acid addition salts of the present invention exist in essentially crystalline form, it is understood that such compounds may exist in partially crystalline or even amorphous form depending on, for example, the conditions under which the solid product forms. These forms are also contemplated by the present invention. It is further understood that certain crystalline compounds may exist in different crystalline forms—a phenomenon known as polymorphism. These individual crystalline forms and mixtures thereof are also contemplated by the present invention. It is understood that the skilled person would be aware of a number of different parameters that may be varied to affect the nature of the solid produced through the action of the acid on the free base of formula I.

The present invention also relates to solvates (including hydrates) of the acid addition salts of formulae II and III. Solvents used for crystallisation may include alcohols (eg methanol, ethanol, i-PrOH), aldehydes, ketones (eg acetone), esters (eg ethyl acetate) and water, each of which may inevitably be to some degree embedded within the salt products. The amount and location of the solvent molecule(s) within the salt product depend on such factors as crystallisation solvent(s), the temperature under which crystallisation occurs, the pressure under which crystallisation occurs, the rate of crystallisation, inter and intra-molecular forces, storage and drying conditions following isolation, etc. Preferably the solvent used to form the salt products is pharmaceutically acceptable.

The present invention also provides solid and liquid pharmaceutical compositions comprising one or both of the salts of the present invention, preferably in a therapeutically effective amount, together with one or more pharmaceutically acceptable solid and/or liquid carriers. As used herein, the term "pharmaceutically acceptable carrier" encompasses such terms as filler, diluent, excipient, additive or encapsulating substance, and may be safely used in topical, local or systemic administration. The pharmaceutically active derivatives of the present invention can be readily formulated with pharmaceutically acceptable carriers well known in the art such as flavouring agents, solubilizers, lubricants, suspending agents, binders, preservatives, tablet disintegrating agents and encapsulating materials. Such carriers enable the compounds of the invention to be formulated in dosage forms such as tablets, powders, cachets, lozenges, pills, capsules, liquids, gels, syrups, slurries, suspensions and the like. These carriers are well known in the art and may include sugars, starches, cellulose and its derivatives, malt, gelatin, magnesium carbonate, magnesium stearate, talc, calcium sulfate, vegetable oils, synthetic oils, polyols, alginic acid, phosphate buffered solutions, emulsifiers, pectin, tragacanth, low melting wax, cocoa butter, isotonic saline and pyrogen-free water.

The surprising properties of the salts of the present invention make them particularly suitable for use in solid pharmaceutical compositions. For example, their lack of hygroscopicity facilitates ease of handling (weighing, transportation, etc), whilst their stability facilitates extended shelf-life following synthesis and isolation. In particular, pharmaceutical compositions for oral use can be obtained by combining the active compounds with solid excipients, optionally grinding the resulting mixture, and processing the mixture of granules, after adding suitable auxiliaries, if desired, to obtain tablets or dragee cores. Suitable excipients include fillers such as sugars (including lactose, glucose, sucrose, mannitol or sorbitol) and cellulose preparations such as maize starch, wheat starch, rice starch, potato starch, gelatin, gum tragacanth, methyl cellulose, hydroxypropylmethyl-cellulose, sodium carboxymethylcellulose as well as polyvinylpyrrolidone (PVP). If desired, disintegrating agents such as cross-linked polyvinyl pyrrolidone, agar, or alginic acid or a salt thereof (such as sodium alginate) may be added. The invention also provides dragee cores comprising suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

According to a preferred embodiment the pharmaceutical composition comprising the acid addition salt of the compound of formula I in accordance with the invention is formulated for oral delivery.

Pharmaceuticals which may be used orally include push-fit capsules made of gelatin, as well as soft, sealed capsules made of gelatin and a plasticiser, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The comparatively high aqueous solubility of each of the salts of the invention makes them suitable for use in pharmaceutical compositions that comprise polar (especially aqueous) solvent(s). In particular, liquid pharmaceutical compositions provided by the invention may contain acceptable diluents and carriers which are familiar to those skilled in the art and include, but are not restricted to, saline, sterile water, ethoxylated and nonethoxylated surfactants, poly(ethylene glycol), poly(propylene glycol), fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, synthetic gums, resins, preserving agents, wax esters, steroid alcohols, triglyceride esters, phospholipids such as lecithin and cephalin, polyhydric alcohol esters, fatty alcohol esters, hydrophilic lanolin derivatives, hydrophilic beeswax derivatives and host molecules such as cyclodextrins (for example α-, β- and/or γ-cyclodextrin) which may modify exposure of parts of the guest molecule (for example the salts of the invention) to solvent.

The compositions of the present invention may also be administered to the respiratory tract as a nasal or pulmonary inhalation aerosol or solution for a nebuliser, or as a microfine powder (preferably with particles of the order of 1 to 10 microns in size or less) for insufflation, alone or in combination with an inert carrier such as lactose, or with other pharmaceutically acceptable excipients. Aerosol formulations include those in which the salt is provided in a pressurized pack with a suitable propellant such as a chlorofluorocarbon (CFC) for examples dichlorodifluoromethane, trichlorofluoromethane, dichlorotetrafluoroethane, carbon dioxide, or other suitable gas. The aerosol may conveniently also contain a surfactant such as lecithin. The dose of the drug may be controlled by provision of a metered valve. The salt may also be provided in a pharmaceutical formulation which forms a gel in the nasal cavity. The powder composition may be presented in unit dose form for example in capsules or cartridges of eg gelatin, or blister packs from which the powder may be administered by means of an inhaler. Accordingly, in yet another preferred embodiment, the pharmaceutical composition comprising the acid addition salt of the compound of formula I in accordance with the invention is formulated for intranasal delivery.

The pharmaceutical compositions of the present invention may provide for the sustained release of the active compound.

Preferably the pharmaceutical compositions of the present invention are present in unit dosage forms.

The pharmaceutical compositions of the present invention may also comprise one or more other therapeutic and/or prophylactic ingredients. The salts of this invention may be useful in combination with known anti-viral or anti-retroviral agents or other pharmaceuticals used in the treatment of viral infections. Representative examples of these additional pharmaceuticals include immunomodulators, immunostimulants, antibiotics and anti-inflammatory agents. Exemplary anti-viral agents include zanamivir, rimantidine, amantidine, ribavirin, AZT, 3TC, (−) FTC, acyclovir, famciclovir, penciclovir, ddI, ddC, ganciclovir, saquanivir, loviride, other non-nucleotide reverse transcriptase (RT) inhibitors and protease inhibitors, antiviral and antireceptor antibodies and receptor analogues, such as ICAM-1. Exemplary immunomodulators and immunostimulants include various interleukins, cytokines and antibody preparations. Exemplary antibiotics include antifungal agents and antibacterial agents. Exemplary anti-inflammatory agents include glucocorticoids and non-steroidal anti-inflammatory compounds.

As used herein, the term "effective amount" relates to an amount of one or more active substances that is effective in producing a desired outcome in a subject in need of treatment or prophylaxis, either in a single dose or as part of a series. Such an effect may be measured, for example, through a decrease in the number of particles of a particular virus or viruses, or by the relief of symptoms within the subject. The effective amount will vary depending upon the health and physical condition of the individual to be treated, the taxonomic group of the subject to be treated, the formulation of the composition, the assessment of the medical situation, and other relevant factors. The quantity of the pharmaceutically active compounds(s) to be administered may depend on the subject to be treated inclusive of the age, sex, weight and general health condition thereof. It is expected that the effective amount will fall in a relatively broad range that can be determined through routine trials. In some instances, administration of an "effective amount" of active may produce a 50% reduction in symptoms and/or number of relevant virus particles in the subject. The dose of active compounds administered to a subject should be sufficient to achieve a beneficial response in the subject over time such as a reduction in, or relief from, symptoms of viral infection. In this regard, precise amounts of the active compound(s) for administration will depend on the judgment of the practitioner. In determining the effective amount of the active compound(s) to be administered, the physician may evaluate the severity of the symptoms associated with viral infection and/or some other means of determining the extent of the viral infection. Formulations containing one hundred (100) milligrams of active ingredient or, more broadly, 0.1 to four hundred (400) milligrams per tablet, are accordingly suitable representative unit dosage forms.

As used herein, the term "subject" or "individual" or "patient", may be used interchangeably, and refer to any subject, preferably a vertebrate subject, and even more preferably a mammalian subject, for whom treatment or prevention is desired. Most preferably the subject is a human in need of treatment or prevention of a virus, preferably of the picornaviridae family, especially HRV.

Accordingly in another aspect the present invention provides a method of treating a picornavirus infection in a subject in need thereof comprising administering a salt of formula II and/or formula III.

In another aspect the present invention provides a method of preventing a picornavirus infection in a subject in need thereof comprising administering a salt of formula II and/or formula III.

In another aspect the present invention provides the use of a salt of formula II and/or formula III in the manufacture of a medicament for the treatment of a picornavirus infection in a subject in need thereof.

In another aspect the present invention provides the use of a salt of formula II and/or formula III in the manufacture of a medicament for the prevention of a picornavirus infection in a subject in need thereof.

The picornavirus infection may be caused by any virus of the family Picornaviridae. Representative family members include human rhinoviruses, polioviruses, enteroviruses including coxsackieviruses and echoviruses, hepatovirus, cardioviruses, apthovirus, hepatitis A and other picornaviruses not yet assigned to a particular genus, including one or more of the serotypes of these viruses. Preferably the invention is used in the prevention or treatment of infection caused by one or more serotypes of rhinovirus.

The terms "treatment" and "treating" as used herein cover any treatment of a condition or disease in a subject, preferably a mammal (non-human mammals or humans), more preferably a human, and includes: (i) inhibiting the viral infection, i.e., arresting its proliferation; (ii) relieving the infection, i.e. causing a reduction in the severity of the infection; or (iii) relieving the conditions caused by the infection, i.e. symptoms of the infection. The terms "prevention" and "preventing" as used herein cover the prevention or prophylaxis of a condition or disease in a subject, preferably a mammal (non-human mammals or humans), more preferably a human and includes preventing the viral infection from occurring in a subject which may be predisposed to infection but has not yet been diagnosed as being infected.

The invention will now be described with reference to some examples. It is to be understood that the particularity of the following description is not to supersede the generality of the preceding description of the invention.

EXAMPLE 1

6-{2-[1-(6-methyl-3-pyridazinyl)-4-piperidinyl]ethoxy}-3-ethoxy-1,2-benzisoxazole phosphate salt [formula III]

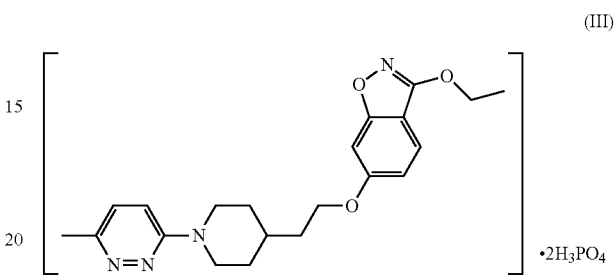

(III)

Free base of formula I (1 kg) was added to isopropanol (24 L). The suspension was heated to reflux, dissolving the base. An aqueous solution of phosphoric acid (81% w/w, 0.63 kg, 2.1 eq) in isopropanol (2.3 L) was heated to 80° C., before being added rapidly, with agitation, to the refluxing solution of the free base. A precipitate formed immediately. The slurry was heated at between 78° C. and 82° C. for 5 minutes before being cooled to room temperature. The solid product was washed with isopropanol (3×10 L) then acetone (3×10 L) before being dried at 40° C. in vacuo to constant mass, affording the title compound as a bright yellow crystalline solid (1.5 kg, 97%).

EXAMPLE 2

6-{2-[1-(6-methyl-3-pyridazinyl)-4-piperidinyl]ethoxy}-3-ethoxy-1,2-benzisoxazole sulfate salt [formula II]

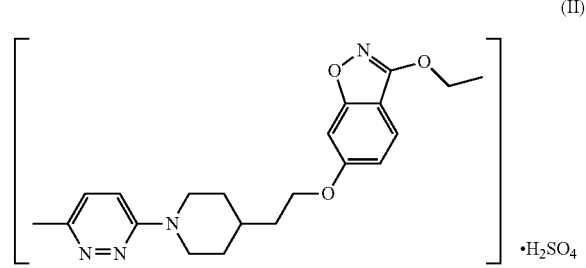

(II)

A solution of the free base of formula I (1 g) in tetrahydrofuran (52 mL) was added to an aqueous solution of sulfuric acid (0.05 M; 52 mL; 1 eq). The mixture turned immediately cloudy. The salt was isolated by slow removal of solvent according to the following pressure reduction program at room temperature:

| Time (h) | Pressure |
|---|---|
| 00:00:00 | 600 mbar |
| 00:30:00 | 600 mbar |
| 01:30:00 | 500 mbar |

-continued

| Time (h) | Pressure |
|---|---|
| 02:30:00 | 400 mbar |
| 05:30:00 | 300 mbar |
| 08:30:00 | 200 mbar |
| 11:30:00 | 100 mbar |
| 14:30:00 | 1 mbar |
| 18:00:00 | 1 mbar |

EXAMPLE 3

Pharmaceutical compositions comprising the salt of formula III were prepared by filling brown size 0 hard gelatin capsules with the salt and made to weight with anhydrous glucose. The compositions of the capsules are summarised in Table 5.

TABLE 5

| Components | Qty/capsule (mg) | | | | | Function |
|---|---|---|---|---|---|---|
| salt of formula III | 10 | 25 | 50 | 100 | 200 | Active drug substance |
| Glucose (anhydrous) | QS | QS | QS | QS | QS | Diluent |
| Brown size 0 hard gelatin capsules | 1 | 1 | 1 | 1 | 1 | Capsule |

QS = a sufficient quantity to meet the pre-determined fill weight.

EXAMPLE 4

X-Ray Crystallography

X-Ray crystal structures were obtained for the monosulfate and bis-dihydrogenphosphate salts after re-crystallisation from methanol.

(i) Monosulfate Salt (Molecular Formula [$C_{21}H_{28}N_4O_3$]($SO_4$))

Six different solvents (ethanol, methanol, acetone, tetrahydrofuran, acetonitrile and 2-propanol) were evaluated for the recrystallisation of the monosulfate salt. Methanol was selected as it showed the best solubility of the salt at elevated temperatures. 20 mg of the monosulfate salt was dissolved in warm methanol at 40° C. and then slowly cooling to room temperature gave rise to the formation of yellow crystals. A yellow crystal was mounted on a Stoe Mark II-Imaging Plate Diffractometer System (Stoe & Cie, 2002) equipped with a graphite-monochromator.

Data collection was performed at −100° C. using Mo-Kα radiation ($\lambda$=0.71073 Å). 180 exposures at 10 min per exposure were obtained at an image plate distance of 135 mm, $\phi$=0° and) <ω<180° with the crystal oscillating through 1° in ω. The resolution was $D_{min}$-$D_{max}$ 0.82-24.00 Å.

The monosulfate salt crystallised in a centrosymmetric monoclinical cell, space group $P2_1/c$. The structure of this compound was solved by directed methods using the program SHELXS-97 (Sheldrick, G. M., Acta Cryst. (2008) A64, 112-122) and refined by full matrix least squares on F (Spek, A. L. J. Appl. Cryst. (2003) 36, 7-13) with SHELXH-97. The N—H hydrogen atoms were derived from Fourier difference maps and then treated as riding atoms while the remaining hydrogen atoms were directly included in calculated positions and treated as riding atoms using SHELXL-97 default parameters. All non-hydrogen atoms were refined anisotropically. No absorption correction was applied. The crystal was only weakly diffracting related to its size (0.50×0.45×0.03 mm). The crystals were obtained as very thin plates. The structure was refined with acceptable standard uncertainties in bond distances and angles.

X-Ray Crystal Data for Monosulfate Salt

Crystal Data

Crystal shape: plate; Crystal colour: yellow; Crystal size: 0.50×0.45×0.03 mm; Empirical formula: $C_{21}H_{28}N_4O_7S$; Formula weight: 480.53; Crystal system: Monoclinic; Space group: P $2_1/c$; Unit cell dimensions: a=22.578(4) A alpha=90 deg.; b=13.175(2) A beta=94.746(15) deg.; c=7.4843(13) A gamma=90 deg.; Volume: 2218.7(7) A^3; Cell refinement parameters: Reflections 1873; Angle range 2.38<theta<21.30;

Z is 4;

Density (calculated) 1.439 g/cm^3; Radiation used MoK\a; Wavelength 0.71073 A; Linear absorption coefficient 0.198 mm$^{-1}$; Temperature 173(2) ° K Data Collection Details Diffractometer STOE IPDS 2; Scan method rotation method; Number of Reflections measured 12038; Number of Independent reflections 2889; Number of observed reflections 1060; Criterion for recognizing >2sigma(I); R(int)= 0.2485; Theta range for data collection 1.79 to 22.50 deg; Index ranges 24<=h<=24, −14<=k<=14, −8<=l<=8; F(000) 1016

Refinement Details

Refinement method Full-matrix least-squares on F$^2$; Final R indices [I>2sigma(I)] R1=0.1022, wR2=0.2222; R indices (all data) R1=0.2264, wR2=0.2816; R1 [=SUM(||Fo|−|Fc||)/SUM|Fo|]; wR^2 {=[SUM(w(Fo^2−Fc^2)^2)/SUM(wFo^4)]^½ }; H- locating and refining Method constr; Number of reflections used 2889; Number of L.S. restraints 4; Number of refined Parameters 298; Goodness-of-fit on F^2 0.892; S {=[SUM w(Fo^2−Fc^2)^2]/(n−p)^½} n=number of reflections; p=Parameters used; calc w=1/[\s^2^(Fo^2^)+(0.1225P)^2^]; where P=(Fo^2^+2Fc^2^)/3; Maximum delta/sigma 0.000; Maximum e-density 0.374 e.A^−3; Minimum e-density −0.538 e.A^−3

Computer Programs used

Data collection program STOE X-AREA; Cell refinement program STOE X-AREA; Data reduction program STOE X-RED; Structure Solving Program SHELXS-97 (Sheldrick, 1990); Structure Refinement Program SHELXL-97 (Sheldrick, 1997)

(ii) Bis-Dihydrogenphosphate Salt Monohydrate (Molecular Formula {[$C_{21}H_{28}N_4O_3$]($H_2PO_4$)$_2$ ($H_2O$)})

Six different solvents (ethanol, methanol, acetone, tetrahydrofuran, acetonitrile and 2-propanol) were evaluated for the recrystallisation of the bis-dihydrogenphosphate salt. Methanol was selected as it showed the best solubility of the salt at elevated temperatures. 20 mg of the monosulfate salt was dissolved in warm methanol at 40° C. and then slowly cooling to room temperature gave rise to the formation of yellow crystals. A yellow crystal was mounted on a Stoe Mark II-Imaging Plate Diffractometer System (Stoe & Cie, 2002) equipped with a graphite-monochromator.

Data collection was performed at −100° C. using Mo-Kα radiation ($\lambda$=0.71073 Å). 180 exposures at 10 min per exposure were obtained at an image plate distance of 135 mm, $\phi$=0° and <ω<180° with the crystal oscillating through 1° in ω. The resolution was $D_{min}$–$D_{max}$ 0.82-24.00 Å.

The bis-dihydrogenphosphate salt crystallised in a centrosymmetric monoclinical cell, space group C2/c. The compound crystallized as a di-cation with two $H_2PO_4^-$ anions and one strongly disordered water molecule. A disorder was found for one of the two anions resulting in partial occupations for atoms O9, O10, O11, O9a, O10a and O11a (occupation 0.5). No hydrogen atoms were found for the $H_2PO_4^-$ anions but they are included in calculations. The disordered and partially occupied water molecules were refined isotropically. No hydrogen atoms were found for the water molecules but they are included in calculations.

The structure of this compound was solved by directed methods using the program SHELXS-97 (Sheldrick, G. M., Acta Cryst. (2008) A64, 112-122) and refined by full matrix least squares on F (Spek, A. L. J. Appl. Cryst. (2003) 36, 7-13) with SHELXH-97. The N—H hydrogen atoms were derived from Fourier difference maps and then treated as riding atoms while the remaining hydrogen atoms were directly included in calculated positions and treated as riding atoms using SHELXL-97 default parameters. All non-hydrogen atoms were refined anisotropically. No absorption correction was applied. The crystal was only weakly diffracting related to its size (0.45×0.40×0.05 mm). The crystals were obtained as very thin plates. The structure was refined with acceptable standard uncertainties in bond distances and angles.

X-Ray Crystal Data for Bis-Dihydrogenphosphate Salt
Crystal Data

Crystal shape: plate; Crystal colour: yellow; Crystal size: 0.45×0.40×0.05 mm; Empirical formula: $C_{21}H_{34}N_4O_{12}P$; Formula weight: 596.46; Crystal system: Monoclinic; Space group: C 2/c; Unit cell dimensions: a=54.964(14) A alpha=90 deg.; b=12.692(2) A beta=91.931(18) deg.; c=7.8918(15) A gamma=90 deg.; Volume: 5502(2) $A^3$; Cell refinement parameters: Reflections. 4485; Angle range 1.48<theta<21.98;

Z is 8;

Density (calculated) 1.440 $g/cm^3$; Radiation used MoK\a; Wavelength 0.71073 A; Linear absorption coefficient 0.226 $mm^{-1}$; Temperature 173(2) K Data Collection Details Diffractometer STOE IPDS 2; Scan method rotation method; Number of Reflections measured 19426; Number of Independent reflections 3608; Number of observed reflections 1416; Criterion for recognizing >2sigma(I); R(int)= 0.2505; Theta range for data collection 1.48 to 22.50 deg; Index ranges $-58<=h<=58, -13<=k<=13, -8<=l<=8$; F(000) 2512

Refinement Details

Refinement method Full-matrix least-squares on $F^2$; Final R indices [I>2sigma(I)] R1=0.0995, wR2=0.2330; R indices (all data) R1=0.2114, wR2=0.2823; R1 [=SUM(||Fo|−|Fc||)/SUM|Fo|]; $wR^2$ {=[ SUM(w(Fo^2−Fc^2)^2)/SUM(wFo^4)]^ ½}; H-locating and refining Method constr; Number of reflections used 3608; Number of L.S. restraints 7; Number of refined Parameters 342; Goodness-of-fit on F^2 0.928; S {=[SUM w(Fo^2−Fc^2)^2]/(n−p)^½} n=number of reflections; p=Parameters used; calc w=1/[\s^2^(Fo^2^)+(0.1225P)^2^]; where P=(Fo^2^+2Fc^2^)/3; Maximum delta/sigma 0.000; Maximum e-density 0.610 e.A^−3; Minimum e-density −0.417 e.A^−3

Computer Programs Used

Data collection program STOE X-AREA; Cell refinement program STOE X-AREA; Data reduction program STOE X-RED; Structure Solving Program SHELXS-97 (Sheldrick, 1990); Structure Refinement Program SHELXL-97 (Sheldrick, 1997)

EXAMPLE 5

Salt Characterisation Methods and Parameters

The salts of the invention were characterised using the following methods and parameters.
Parameters for Raman Measurements
Spectrometer: Bruker RFS 100/S Raman spectrometer
Excitation Laser power: 400 mW
Resolution: 2 $cm^{-1}$
No. of scan: 128
Acquisition range: 3300-0 $cm^{-1}$
Aperture: 5.0 mm
Type of vial: RPD 96 well plate format glass vial or RPD 96 well plate format glass vial with FEP lining.
Sample position: optimized to best signal intensity
Spectrum pre-treatment: Linear baseline correction, normalisation.
Parameters for NIR Measurements
Spectrometer: Brucker Vector 22 NIR spectrometer
Resolution: 2 $cm^{-1}$
No. of scan: 64
Acquisition range: 833-2500 nm.
Aperture: 5.0 mm
Type of vial: RPD 96 well plate format glass vial
Spectrum pre-treatment: Linear baseline correction.
CCD-Picture Acquisition
Camera: Sony XCD-C710CR
Objective: Navitar Precision Eye (Body tube art. no. 1-61449 with attachments 1.33 X (art. no. 1-41448) and 0.5 X (art. no.; 1-60110).
X-Ray Powder Diffraction
Spectrometer: Stoe Stadip diffractometer
Detector/geometry: Position sensitive detector/Debye-Scherrer geometry.
X-Ray source: Cu K alpha; Measurement mode: Transmission in 0.5 mm capillary
Elemental Analysis
The following methods were used for the determination of the elemental composition:
C, H, N: Thermal decomposition and quantitative determination of the flue gas stream (Instrument Leco-900)
Cl: Ion chromatographic determination after Schoniger digestion.
S: Thermal decomposition and quantitative determination of the flue gas stream using an IR detector (Instrument LECO-CHN-932)
P: Photometric determination after microwave digestion.
DSC Analysis
The DSC analyses were performed on a Mettler Toledo differential scanning calorimeter with a heating rate of 5° C. per minute.
Solubility Determination
Approximately 10 mg of the acid addition salt were equilibrated for 24 hours at 25° C. with deionised water. The suspension was filtered, the content of the free base was determined by HPLC and the pH of the saturated solutions was measured.
HPLC Analysis
A test solution of the acid addition salt was prepared by dissolving 10.0 mg of the salt in acetonitrile:ethanol=1:1 and diluted to a concentration of 1.0 mg/mL.

Chromatograph: TSP-
Detector Spectra-Physics SP877 XR

-continued

| Column: | Layer thickness: 8 mm.<br>Detection wavelength: 230 nm (UV detection)<br>Output voltage: 1 V<br>Nucleosil C18<br>Particle size: 5 μm<br>Column length: 250 mm<br>Column i.d.: 4.0 mm |
|---|---|
| Column temperature: | room temperature |
| Size of sample: | 10 μl of reference/test solution |
| Flow rate: | 1.0 ml/minute |

| Gradient program 1: | Time<br>[minutes] | 0.1% aqueous<br>phosphoric acid [%] | Acetonitrile<br>[%] |
|---|---|---|---|
| | 0 | 70 | 30 |
| | 35 | 1 | 99 |
| | 36 | 70 | 30 |
| | 41 | 70 | 30 |

| Evaluation: | Calculation of area-% |
|---|---|

Exemplary HPLC Assay Data for Bis-Dihydrogenphosphate Salt
Chromatographic Conditions

| Equipment: | HPLC system fitted with a UV Detector |
|---|---|
| Column: | Waters Symmetry, C8, 5 μm, 150 mm × 3.9 mm |
| Column temperature: | 25° C. |
| Detector wavelength: | 265 nm |
| Flow rate: | 1.0 mL/min |
| Injection volume: | 10 μL |
| Mobile phase: | 0.1M $KH_2PO_4$ (pH 3.0):Methanol (45:55) |
| Run time: | 30 minutes |
| Diluent: | Mobile phase |
| Needle wash: | Methanol (100%) |

Under these conditions, the retention time for the bis-dihydrogenphosphate salt is approximately 9-11 mins.

Figure 9:
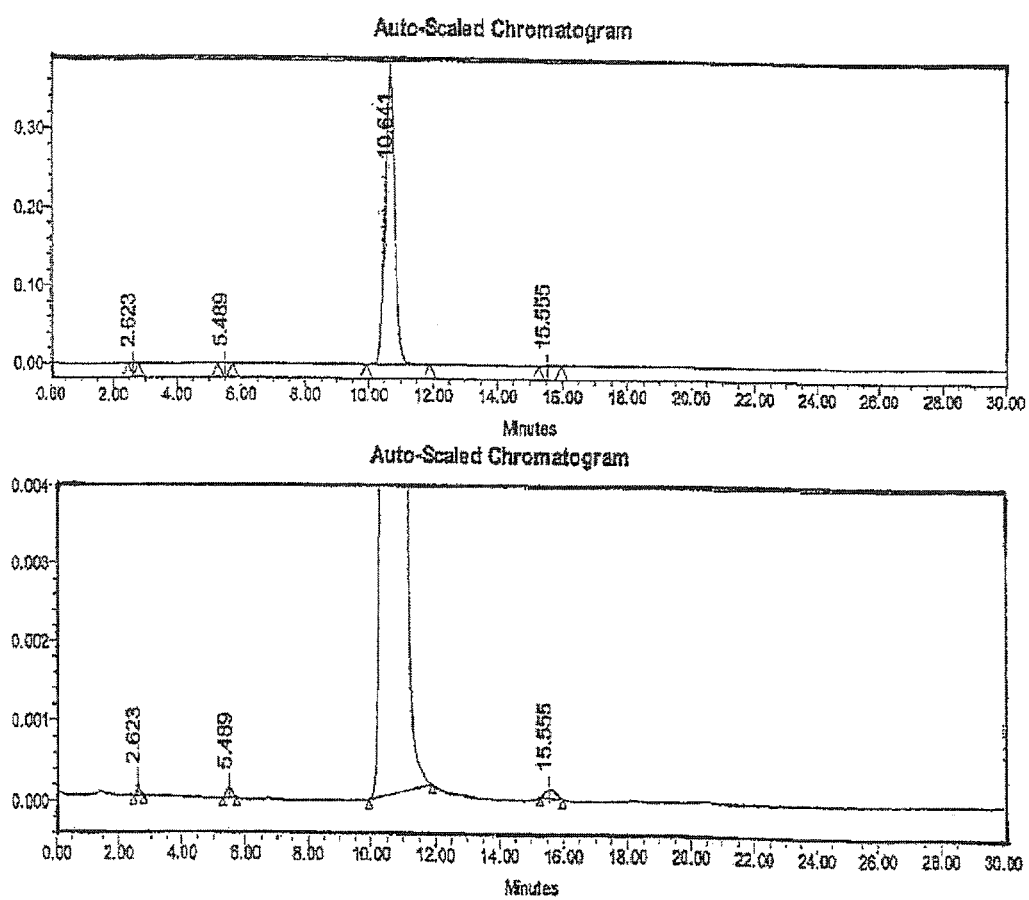
FIG. 9 shows a typical HPLC chromatogram for the bis-dihydrogenphosphate salt in accordance with a preferred embodiment of the invention. It may be assumed that the salt will dissociate, at least to some degree, during analysis under these conditions.

An exemplary HPLC chromatogram is shown in FIG. 9 having the following peak results:

| Name | Int Type | RT | Height | Area | % Area |
|---|---|---|---|---|---|
| | BB | 2.623 | 180 | 1311 | 0.02 |
| | BB | 5.489 | 135 | 1697 | 0.02 |
| Bis-<br>dihydrogen-<br>phosphate salt | BB | 10.641 | 366923 | 7581975 | 99.93 |
| | bb | 15.555 | 113 | 2575 | 0.03 |

Stability

Approximately 30 mg of the salt was stored in a 96 well glass vial for four weeks under the following conditions:
25° C./dry
25° C./75% relative stability
40° C./dry
40° C./75% relative stability During storage of the test samples, NIR and Raman spectra were acquired (non-invasively) at pre-selected time points. The Raman and NIR spectra data sets were analysed with respect to hygroscopicity (NIR), morphological (NIR and Raman) and chemical changes of the test substance. HPLC analysis of the test substances was performed at the end of the storage period.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or know matter forms part of the common general knowledge in the field of endeavour to which this specification relates.

The invention claimed is:

1. A method of inhibiting rhinovirus activity in a human in need thereof, comprising the step of administering to said human an effective amount of a crystalline form of 6-{2-[1-(6-methyl-3-pyridazinyl)-4-piperidinyl]ethoxy}-3-ethoxy-1,2-benzisoxazole bis-dihydrogenphosphate salt (1:2), wherein the crystalline form has an x-ray powder diffraction pattern with 2θ peaks (±0.2°) at 3.3°, 6.7°, 12.8°, 13.3°, 14.1°, 19.2°, 20.0°, 21.1° and 22.4°.

2. The method of claim 1 further comprising the step of administering to said human an anti-viral agent, an anti-retroviral agent, and/or a pharmaceutical for treatment of viral infections.

3. The method of claim 1 wherein the crystalline form is administered as a pharmaceutical composition, wherein the pharmaceutical composition comprises the crystalline form and a pharmaceutically acceptable carrier.

4. The method of claim 3 wherein the pharmaceutical composition is formulated for intranasal delivery.

5. The method of claim 3 wherein the pharmaceutical composition is in a unit dosage form.

6. The method of claim 3 wherein the pharmaceutical composition further comprises glucose.

7. The method of claim 3 wherein the pharmaceutical composition provides for sustained release of the crystalline form.

8. The method of claim 3 wherein the pharmaceutical composition is in the form of a tablet, powder, cachet, lozenge, pill or capsule.

9. The method of claim 3 wherein the pharmaceutical composition is in the form of a liquid, gel, syrup, slurry or suspension.

10. The method of claim 3 wherein the pharmaceutical composition is in the form of an inhalation aerosol, nebulizer solution, or microfine insufflation powder.

11. The method of claim 3 wherein the pharmaceutical composition further comprises an anti-viral agent, an anti-retroviral agent, and/or a pharmaceutical for treatment of viral infections.

* * * * *